(12) United States Patent
Taylor

(10) Patent No.: US 11,578,781 B2
(45) Date of Patent: Feb. 14, 2023

(54) RETAINING DEVICE AND METHOD OF USING THE SAME

(71) Applicant: Kevin D. Taylor, Colorado Springs, CO (US)

(72) Inventor: Kevin D. Taylor, Colorado Springs, CO (US)

( * ) Notice: Subject to any disclaimer, the term of this patent is extended or adjusted under 35 U.S.C. 154(b) by 0 days.

(21) Appl. No.: 15/687,977

(22) Filed: Aug. 28, 2017

(65) Prior Publication Data

US 2017/0356524 A1    Dec. 14, 2017

Related U.S. Application Data

(63) Continuation of application No. 13/367,208, filed on Feb. 6, 2012, now Pat. No. 9,746,052.

(60) Provisional application No. 61/440,272, filed on Feb. 7, 2011.

(51) Int. Cl.

| | |
|---|---|
| *F16G 11/00* | (2006.01) |
| *F16G 11/02* | (2006.01) |
| *F16G 11/14* | (2006.01) |
| *F16L 3/12* | (2006.01) |
| *A61M 5/14* | (2006.01) |
| *A61B 17/08* | (2006.01) |
| *A61B 17/22* | (2006.01) |
| *A61B 46/23* | (2016.01) |
| *A61B 90/50* | (2016.01) |

(52) U.S. Cl.
CPC ............ *F16G 11/00* (2013.01); *A61M 5/1418* (2013.01); *F16G 11/02* (2013.01); *F16G 11/146* (2013.01); *F16L 3/1218* (2013.01); *A61B 17/085* (2013.01); *A61B 46/23* (2016.02); *A61B 90/50* (2016.02); *A61B 2017/22038* (2013.01); *Y10T 29/49826* (2015.01)

(58) Field of Classification Search
CPC ........ F16G 11/02; F16L 3/1218; A61B 46/23; A61B 2046/234; A61B 90/50; A61B 17/085; A61B 2017/22038; A61M 5/1418
USPC ...................................................... 248/74.1
See application file for complete search history.

(56) References Cited

U.S. PATENT DOCUMENTS

| | | | |
|---|---|---|---|
| 263,624 A | | 8/1882 | Sweetland |
| 1,389,304 A | * | 8/1921 | Holmes .................... A41F 11/02 24/21 |
| 2,135,134 A | * | 11/1938 | Ehlers ................ B65D 73/0021 206/728 |

(Continued)

FOREIGN PATENT DOCUMENTS

JP          09-239039          9/1997

*Primary Examiner* — Kimberly T Wood
(74) *Attorney, Agent, or Firm* — Messner Reeves LLP; Scott J. Hawranek

(57) ABSTRACT

A retaining device configured for retaining at least one medical device adjacent to a supporting surface. The retaining device includes a plate shaped holding portion defining a peripheral edge, a slot extending from the peripheral edge defining a loading channel, and communicating with an internal holding area. The internal holding area is dimensioned to accept the largest medical device the retaining device is configured to be used with. An attachment mechanism is connected to the holding portion to secure the retaining device to a supporting surface. A section of medical device may be inserted into and along the loading channel to enter the holding area and be retained within.

20 Claims, 5 Drawing Sheets

(56) References Cited

U.S. PATENT DOCUMENTS

| | | | | |
|---|---|---|---|---|
| 2,472,028 A * | 5/1949 | Son | A61L 2/26 | |
| | | | 422/310 | |
| 3,286,713 A * | 11/1966 | Kurtz | A61F 13/00021 | |
| | | | 128/207.14 | |
| 3,696,920 A * | 10/1972 | Lahay | A61B 50/20 | |
| | | | 128/DIG. 26 | |
| 3,702,612 A | 11/1972 | Schlesinger | | |
| 4,023,758 A * | 5/1977 | Yuda | H02G 3/32 | |
| | | | 248/73 | |
| 4,074,397 A * | 2/1978 | Rosin | A61M 25/02 | |
| | | | 128/DIG. 15 | |
| 4,163,372 A * | 8/1979 | Frye | F16L 3/223 | |
| | | | 174/175 | |
| D263,624 S | 3/1982 | Stenzler | | |
| 4,520,518 A * | 6/1985 | Reaser | A47C 21/022 | |
| | | | 24/72.5 | |
| 4,606,735 A * | 8/1986 | Wilder | A61M 25/02 | |
| | | | 128/DIG. 26 | |
| 4,654,026 A * | 3/1987 | Underwood | A61M 5/1418 | |
| | | | 128/DIG. 26 | |
| 4,765,576 A * | 8/1988 | Peled | H02G 3/0456 | |
| | | | 248/49 | |
| 4,793,483 A * | 12/1988 | Holmes | A61G 7/0503 | |
| | | | 206/210 | |
| 4,794,660 A * | 1/1989 | Hawkrigg | A47C 21/022 | |
| | | | 24/72.5 | |
| 4,795,121 A * | 1/1989 | Comito | F21S 4/10 | |
| | | | 211/26 | |
| 4,795,429 A * | 1/1989 | Feldstein | A61J 1/1406 | |
| | | | 604/80 | |
| 4,901,212 A * | 2/1990 | Prickett | F21V 21/08 | |
| | | | 362/145 | |
| 4,905,131 A * | 2/1990 | Gary | F21S 4/10 | |
| | | | 248/315 | |
| 4,971,271 A * | 11/1990 | Sularz | A61M 5/1418 | |
| | | | 248/229.13 | |
| 4,974,128 A * | 11/1990 | Prickett | F21V 21/08 | |
| | | | 362/145 | |
| 4,988,062 A * | 1/1991 | London | A61G 7/0503 | |
| | | | 128/DIG. 26 | |
| 5,102,399 A * | 4/1992 | Chu | A61M 1/0045 | |
| | | | 138/106 | |
| 5,323,992 A | 6/1994 | Sifers et al. | | |
| 5,361,756 A * | 11/1994 | Cernosek | F16L 3/2235 | |
| | | | 248/51 | |
| 5,387,177 A * | 2/1995 | Dunn | A61G 7/05715 | |
| | | | 128/897 | |
| D369,957 S | 5/1996 | Blanton | | |
| 5,533,696 A | 7/1996 | Laughlin et al. | | |
| 5,544,031 A * | 8/1996 | Blanton | F21V 19/007 | |
| | | | 248/205.1 | |
| D427,893 S | 7/2000 | Lappin et al. | | |
| 6,375,006 B1 | 4/2002 | Samuels | | |
| 6,375,017 B1 * | 4/2002 | Schattner | A61M 5/1418 | |
| | | | 211/70 | |
| 6,427,952 B2 * | 8/2002 | Caveney | F16L 3/23 | |
| | | | 248/68.1 | |
| 6,850,687 B2 | 2/2005 | Lavoie | | |
| 6,951,324 B2 * | 10/2005 | Karamanos | F24D 19/02 | |
| | | | 248/300 | |
| 7,098,406 B1 * | 8/2006 | Hammonds | B65H 75/06 | |
| | | | 174/135 | |
| D542,907 S | 5/2007 | Isomura et al. | | |
| 7,229,051 B2 | 6/2007 | Mailhot, Jr. | | |
| 7,850,595 B2 * | 12/2010 | White | A61G 7/0503 | |
| | | | 600/22 | |
| 9,746,052 B2 * | 8/2017 | Taylor | F16G 11/00 | |
| 2001/0019091 A1 | 9/2001 | Nakanishi | | |
| 2001/0030267 A1 * | 10/2001 | Caveney | F16L 3/23 | |
| | | | 248/68.1 | |
| 2003/0132352 A1 * | 7/2003 | Weaver | A61G 7/0503 | |
| | | | 248/68.1 | |
| 2003/0168868 A1 * | 9/2003 | Bierlein | B65D 33/14 | |
| | | | 292/307 A | |
| 2003/0222185 A1 * | 12/2003 | Rubenstein | F16L 3/003 | |
| | | | 248/68.1 | |
| 2004/0073233 A1 * | 4/2004 | Jannot | A61B 17/06061 | |
| | | | 606/148 | |
| 2004/0113028 A1 * | 6/2004 | Grendahl | H02G 3/32 | |
| | | | 248/68.1 | |
| 2005/0103949 A1 * | 5/2005 | Ross | A61M 5/1418 | |
| | | | 248/68.1 | |
| 2005/0189453 A1 * | 9/2005 | DeGuevara | H02G 3/305 | |
| | | | 248/68.1 | |
| 2006/0180714 A1 * | 8/2006 | Mailhot | A61M 5/1418 | |
| | | | 248/65 | |
| 2006/0237597 A1 * | 10/2006 | D'Andria | A61M 5/1418 | |
| | | | 248/68.1 | |
| 2007/0045480 A1 * | 3/2007 | Yu | B60R 16/0215 | |
| | | | 248/51 | |
| 2009/0283645 A1 * | 11/2009 | Nikayin | F16L 3/1218 | |
| | | | 248/68.1 | |
| 2010/0301176 A1 * | 12/2010 | Werner | F16L 3/01 | |
| | | | 248/68.1 | |

* cited by examiner

RETAINING DEVICE AND METHOD OF USING THE SAME

This application is a continuation of U.S. patent application No. 13/367,208 filed on Feb. 6, 2012, which claims the benefit of U.S. Provisional Patent Application No. 61/440,272, filed on Feb. 7, 2011, each of which are hereby incorporated by reference for all purposes as if fully set forth herein.

BACKGROUND OF THE INVENTION

Field of the Invention

The present invention relates to retaining devices and, more specifically, retaining devices for securing medical wires, catheters, guidewires, electrical lines, cables, tubing and other elongated members during medical procedures.

Discussion of the Related Art

Guidewires and catheters are used in a variety of different medical procedures such as, angiographic, endovascular, or surgical procedures. Guidewires are typically used to position catheters in a body lumen, for example arteries, veins or natural orifices within a mammal. The leading end portion of the guidewire is typically introduced into the body through an incision or natural orifice and then advanced to the treatment area. A catheter can be threaded over the guidewire and advanced over the guidewire to the treatment area. A single guidewire can be used to deliver multiple catheters to the treatment area within the body lumen. This is normally accomplished by withdrawing and removing the first catheter from the wire while leaving the leading edge of the wire in place within the body lumen, and then threading a second catheter over the wire and advancing down to the treatment site. Multiple guidewires and catheters can be inserted into the body lumen at the same time.

When the guidewire or a guidewire and catheter combination is placed within the body lumen, a loose trailing end portion extends out of the patient from the entry point. This trailing end portion can be difficult to manage and requires special attention from the medical staff to ensure it does not become contaminated, tangled or confused with other wires in the procedural area.

Therefore, a device and method for retaining the trailing end of guidewires and catheters is desired.

SUMMARY OF THE INVENTION

Accordingly, this invention is directed towards a retention device and method of using the same that substantially obviates one or more of the problems due to limitations and disadvantages of the related art.

An advantage of the invention is to provide an apparatus to securely retain a medical wire to a medical surface while providing ease of loading and removal of the medical wire from the apparatus.

Yet another advantage of the invention is to provide a simple and secure mechanism to attach an apparatus to a surface.

Still yet another advantage of the invention is to provide a retention device that allows a guide and catheter exchanges without having to remove the guidewire or catheter from the retention device. Additional features and advantages of the invention will be set forth in the description which follows, and in part will be apparent from the description, or may be learned by practice of the invention. The objectives and other advantages of the invention will be realized and attained by the structure particularly pointed out in the written description and claims hereof as well as the appended drawings.

To achieve these and other advantages and in accordance with the purpose of the present invention, as embodied and broadly described, an aspect of the invention is directed towards a retaining device for securing a medical apparatus during a medical procedure. The retaining device includes a base portion and a holding portion arranged at a predetermined angle from the base portion. The holding portion includes a peripheral edge including a slot extending from the peripheral edge defining a loading channel and communicating with an internal holding area. The internal holding area is dimensioned to accept the medical apparatus via the loading channel. An attachment mechanism is configured to secure the base portion to a supporting surface, e.g., cloth, medical gown, surgical drape, table or other substrate.

Another aspect of the invention is directed towards a method of using a retaining device to secure a medical apparatus to a predetermined location. The method includes attaching a retaining device to a substrate. The retaining device includes a loading channel and a holding area. Opening the loading channel of the retaining device and arranging a portion of the medical apparatus through the loading channel into a holding area of the retaining device.

Yet another embodiment of the invention is directed towards a medical kit and instructions for use. The medical kit includes a retaining device according to any embodiment of the invention.

It is to be understood that both the foregoing general description and the following detailed description are exemplary and explanatory and are intended to provide further explanation of the invention as claimed.

BRIEF DESCRIPTION OF THE DRAWINGS

The accompanying drawings, which are included to provide further understanding of the invention, are incorporated in and constitute a part of this specification. They illustrate embodiments of the invention and together with the description serve to explain the principles of the invention.

In the drawings.

DETAILED DESCRIPTION OF THE ILLUSTRATED EMBODIMENTS

Figure 1:
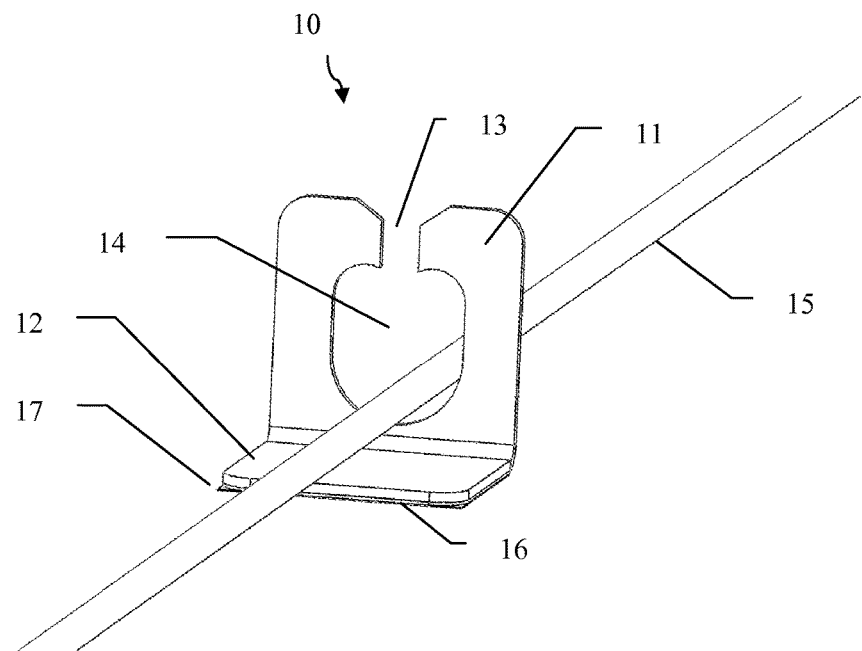
FIG. 1 is a perspective view of a retaining device according to an embodiment of the invention.

An aspect of the invention is directed towards retaining devices and, more specifically, to retaining devices for securing a medical device, e.g., medical wires, catheters, guidewires, electrical lines, cables, tubing and other elongated members. The expression "medical device" is used herein as including all kinds of elongated members used during medical procedures, in particular catheters and guidewires.

In one embodiment, the retaining device for retaining at least one medical device adjacent to a supporting surface includes a plate shaped holding portion defining a peripheral edge, a slot extending from the peripheral edge defining a loading channel, and communicating with an internal holding area. The internal holding area is dimensioned to accept the largest medical device configured to be used with the retaining device. An attachment mechanism is connected to the holding portion to secure the retaining device to a supporting surface. A section of medical device may be inserted into and along the loading channel to enter the holding area and be retained within.

In one embodiment, the holding portion is connected to a plate shaped base portion with an adhesive coating for securing the retaining device to a supporting surface.

In one embodiment, the holding portion is flexible and a portion of the loading channel is dimensioned to be smaller than the smallest medical device that is configured to be used with the retaining device. A portion of the medical device enters through the channel into the internal holding area. In this embodiment, this is accomplished by flexure of the holding portion thus permitting entry of a portion of the medical device into the holding area.

In one embodiment, the holding portion is connected to a plate shaped base portion with an integral feature for securing the device to a supporting surface, e.g., a sheet or drape. The integral feature may be an adhesive, a square or rectangular tab cut from the base portion, or other mechanism. Another mechanism may include a slot dimensioned as a compressive fit as described with reference to U.S. Pat. No. 7,229,051, which is hereby incorporated by reference as if fully set forth herein.

In one embodiment, the retaining device is a one-piece structure and the holding portion is separated from the base portion by a bend or fold in the device. The bend or fold may have an angle in range from about 5 degrees to about 175 degrees, more preferably from about 30 degrees to about 150 degrees and most preferably from about 75 degrees to about 115 degrees.

In one embodiment, the holding portion has multiple slots within the holding area to provide aid in organization of multiple medical devices. Moreover, the shape of the holding portion may be any geometric configuration, e.g., a circle, square, triangle, tear drop, dual tear drop and/or combinations of the same.

In one embodiment, the holding portion is flexible and a portion of the loading channel is dimensioned to be smaller than the smallest medical device that is configured to be used with the retaining device. The holding portion along each edge of the loading channel is angled away from the plane of the holding portion. Medical device entry into the channel produces flexure of the angled channel and the holding portion thus permitting entry into the holding area.

In one embodiment, a retaining device for securing a medical apparatus during a medical procedure includes a base portion and a holding portion arranged at a predetermined angle from the base portion. The holding portion includes a peripheral edge including a slot extending from the peripheral edge defining a loading channel and communicating with an internal holding area. The internal holding area is dimensioned to accept the medical apparatus via the loading channel. An attachment mechanism is configured to secure the base portion to a supporting surface, e.g., cloth, medical gown, table or other substrate.

In one embodiment, a method of using a retaining device to secure a medical apparatus to a predetermined location includes attaching a retaining device to a substrate. The retaining device includes a loading channel and a holding area. Opening the loading channel of the retaining device and arranging a portion of the medical apparatus through the loading channel into a holding area of the retaining device.

In one embodiment, a medical kit includes a retaining device according to any embodiment of the invention and instructions for use. The retaining device includes a base portion, a holding portion arranged at a predetermined angle from the base portion having a peripheral edge including a slot extending from the peripheral edge defining a loading channel. The loading channel is in communication with an internal holding area. The internal holding area is dimensioned to accept the medical apparatus. An attachment mechanism is configured to secure the base portion to a supporting surface. A portion of medical apparatus may be inserted into and along the loading channel to enter the holding area and be retained within In addition to being easy to insert, remove, and securely retain medical devices, and secure the retaining device to various surfaces encountered during medical procedures, this invention allows the insertion and withdrawal of catheters over retained guidewires during interventional procedures. This is important as removing the guidewire from the retaining device during a catheter removal or insertion adds additional risk to the guidewire or catheter falling from the procedural area and becoming contaminated. It also allows for placement of the retaining device further from the catheter insertion point, thus adding more support where it is needed, near the end of the guidewire. The one-piece flat plate construction with a fold or living hinge separating the holder and base portions has the advantage of economical manufacturing, a surface for printing measurement guides and instructions, and increased utility as the user can bend the device to any angle desired.

Reference will now be made in detail to an embodiment of the present invention, example of which is illustrated in the accompanying drawings.

FIG. 1 shows a retaining device 10 according to an embodiment of the invention. The retaining device 10 is configured to retain medical wires or other surgical instruments. In the embodiments shown in the drawings, medical device retaining device 10 is generally a holding portion 11 attached to a base portion 12. Base portion 12 is generally a plate shaped structure, of rectangular shape, for example, and forms the member of the medical device retaining device 10 will rest upon. Holding portion 11 is generally placed at a right angle to base 12, however, it may be configured at an angle within the range from about 0 to 180 degrees during use or transport. For example, it may be advantageous to fold flat at about a 0 degree or 180 degree for product packaging or during the procedure when device in not in use.

In one embodiment, the folding may be accomplished with a living hinge between the base portion and the holding portion. The living hinge may be produced by thinning or reducing the amount of material at the desired bend point. Living hinges are most commonly used in plastics and can be formed by molding, cutting, stamping, perforating and/or thinning a portion of the material at the fold, thereby creating a living hinge. In a preferred embodiment, the product would be manufactured and shipped flat and during use would be folded at the living hinge to the desired orientation. During use the preferred range is from about 75 degrees to about 115 degrees, and more preferably between about 85 degrees to about 95 degrees. In a preferred embodiment, the retaining device 10 is a one-piece construction, where the holding portion and base portion are separated by a bend and are generally orthogonal to each other.

Holding portion 11 includes a plate shaped structure with a slot extending from the upper periphery and defining a loading channel 13, and communicating with an internal holding area 14. A portion of medical device 15 may be inserted via a loading channel at the periphery of the holder portion 11 and into the holding area 14. Once in the holding area 14 the medical device is substantially retained. In this embodiment, the width of the loading channel 13 is configured to accept the largest size medical device anticipated so that medical device insertion or removal has no resistance. That is, the width is configured for a gauge wire in a range from about 0.015 inches to about 0.125 inches. This embodiment relies on gravity and design of the holding portion to retain the medical device 15 in the holding area 14. The holding area 14 is sized to accept the largest medical device and also allow any attachments to the medical device to pass completely through the holding area. For example, a typical catheter will have a shaft diameter of 1.5 millimeters (mm), however the trailing end of the catheter may have a fluid connection fitting with a width of 10 mm and connected to the fitting may be a hemostasis valve with a width of 5 cm. Thus in this example the holding area would be dimensioned to allow the 5 cm hemostasis valve to pass completely through. In one embodiment, the holding area may have an area in the range from about 0.05 inches$^2$ to about 28 inches$^2$, a preferred range from about 0.2 inches$^2$ to about 20 inches$^2$, and a most preferred range from about 0.7 inches$^2$ to about 7 inches$^2$.

In this embodiment, the base 12 contains an adhesive securing mechanism 16 for connecting retaining device 10 to a supporting surface. For example, the adhesive is a pressure sensitive adhesive 16 covering a substantial portion of the bottom of the base portion 12. Adhesive 16 is covered with a protective, peel-off backing 17 until use. Other securing mechanisms as described herein may also be used.

Figure 2A:
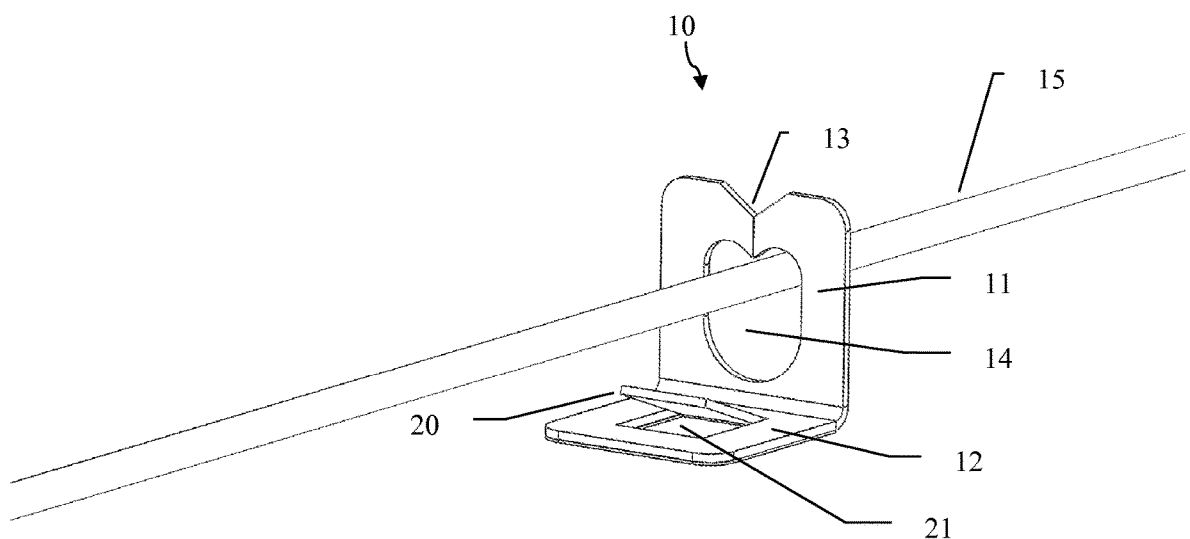
FIG. 2A is a perspective view of another embodiment of the invention.

FIG. 2A shows another embodiment of the invention. Referring to FIG. 2A, the retaining device 10 includes a holding portion 11 having at least a portion of the loading channel with a width of less than the smallest medical device 15 anticipated to be used with the device. In one embodiment, at least a portion of the loading channel may have a width of about 0 inches or less to about 0.5 inches or greater. This embodiment adds more security to retain the medical device 15 in the holding area 14. In order for the wire 15 to move through the channel 13 a portion of the holding portion 11 must flex and allow the channel 13 to open and accept the medical device 15. The flex of the holder portion 11 is controlled by the cross-sectional area, height and modulus of the holder portion. By way of example, FIG. 3 shows flexing of a portion of the holding portion 11 to allow a medical device 15 to be inserted into holding area 14. That is, one side of the holder portion 11 is flexed forward until the medical device 15 can drop in the holding area 14. Flexure of the holder portion 11 occurs either by pushing forward with the medical device 15 when in contact with the holder portion 11 or by pushing manually with a finger. After loading, the holder portion 11 returns to the shape shown in FIG. 2 and the medical device is retained. In one embodiment, the materials used in various features of the device may include a material such as thermoplastic, metal, alloy, plastic, polypropylene (PP), polyethylene (PE), polyethylene terephthalate (PETG), acrylonitrile butadiene styrene (ABS), nylon, polybutylene terephthalate (PBT), styrene, polycarbonate, polytetrafluoroethylene (PTFE), fluorinated ethylene propylene (FEP), polyurethane, acetal, stainless steel, aluminum, steel, copper, brass, nitinol, and combinations of the same.

The medical device 15 can be removed by manually flexing the holder portion 11 to open the loading channel 13. Flexure to open the loading channel 13 can occur by multiple or combination ways, for example, one or both sides of the holder portion 11 could be twisted, or one or both sides of the holder portion could flex laterally, or one or both sides of the holder portion 11 could be flexed forward or backwards.

Also shown in FIG. 2A, the securing mechanism for retaining device 10 is configured to attach to a bed sheet, a medical drape or gown. In this embodiment, base 12 includes an integral rectangular or square tab 20 that has been cut from the base. The tab 20 has three sides and a bend on the remaining side connected to base 12 and angling up from the base. Below the tab 20 is an orifice 21 of corresponding shape, e.g., rectangle, in the base approximately the same size as the tab 20. Any geometrical shape of the tab may be utilized, e.g., triangle, semi-circle, multiple peaks, and the like. Moreover, the tab 20 may include protrusions, e.g., barbs, to aid in securing to the bed sheet, drape or gown.

Figure 3:
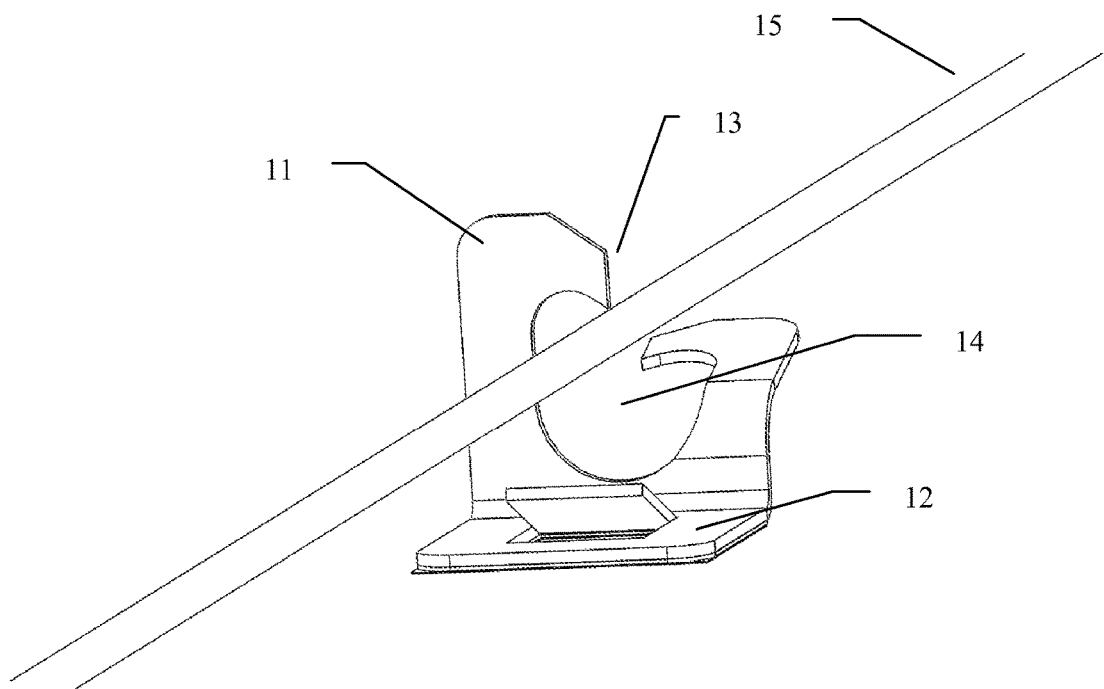
FIG. 3 is an alternate perspective view of the embodiment shown in FIG. 2A.
Figure 4:
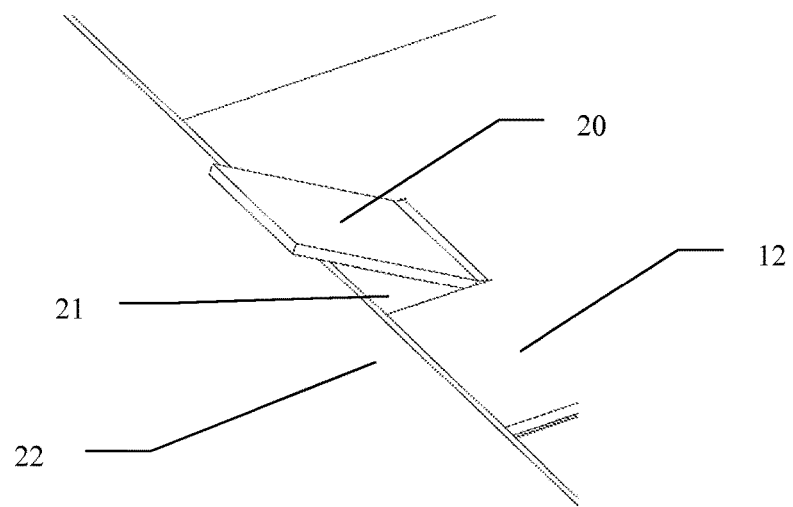
FIG. 4 is a partial, perspective view of the sheet securing feature of the embodiment shown in FIG. 2A.
Figure 5:
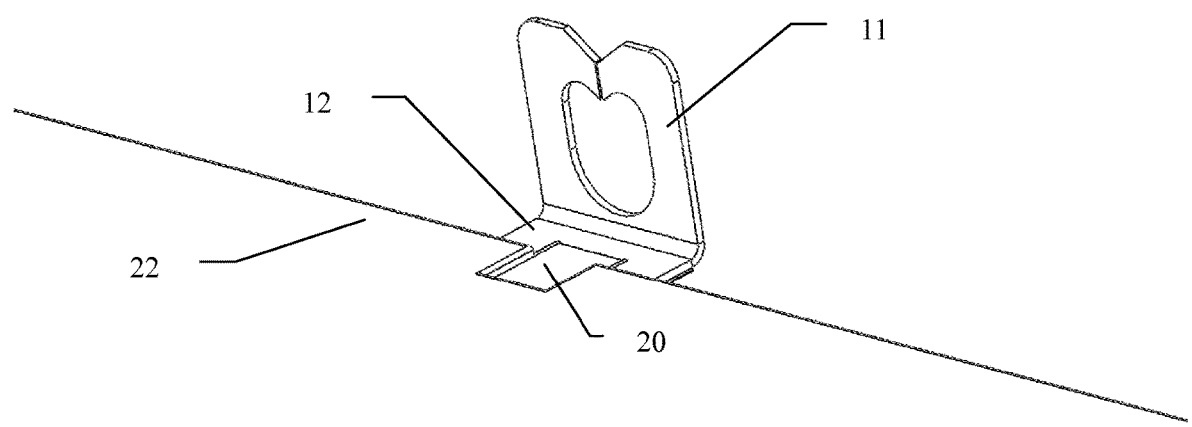
FIG. 5 is a partial, perspective view of the sheet securing feature of the embodiment shown in FIG. 2A.
Figure 6:
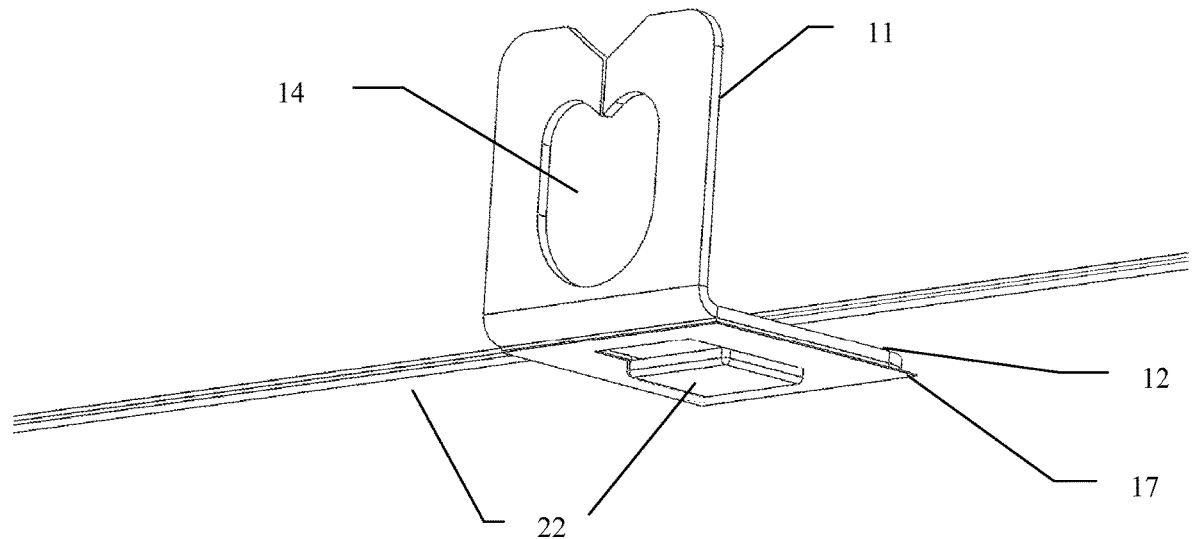
FIG. 6 is a perspective bottom view of the sheet securing feature of the embodiment shown in FIG. 2A.

FIG. 4 shows an edge or folded edge of a sheet 22 placed over the base 12 and under the tab 20. To secure the retaining device 10 to the sheet 22, the tab is pushed down and through the orifice 21 and slightly below the plane of the base, wedging and locking the sheet 22 between the tab 20 and orifice 21. FIGS. 5 and 6 show the sheet 22 in the locked position as viewed from above and below. This embodiment provides a simple, secure mechanism for securing the retaining device to a sheet, drape, or gown. To disengage the sheet 22, push the tab 20 back out the other direction from the bottom of the base 12. As shown in FIGS. 2-6, an advantage of this securing means is that it can be combined with the adhesive means 16 to provide increased utility for securing to many different surfaces. In addition, other securing mechanisms may be utilized, for example, a securing device as described in U.S. Pat. No. 1,389,304, which is hereby incorporated by reference as if fully set forth herein.

Figure 2B:
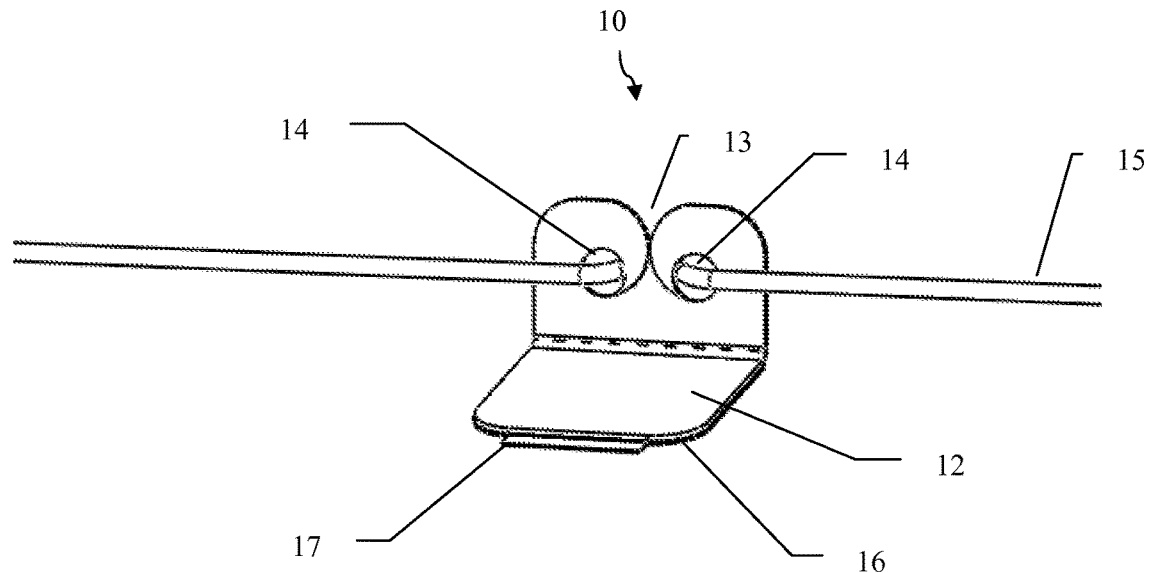
FIG. 2B is a perspective view of another embodiment of the invention.

FIG. 2B, shows another embodiment of the invention. Referring to FIG. 2B, the retaining device 10 is described with reference to FIG. 2A except the internal holding area 14 has a different geometric pattern. In this embodiment, the internal holding area 14 includes two separate spaces. The loading channel 13 splits into two about halfway between the peripheral edge of the holder portion 11 and the bottom of the spaces, each communicating with holding area 14. The advantage of the embodiment is that it allows retention of multiple devices separately and also allows for a retention of a flexible medical device in a longitudinal fashion, as shown in FIG. 2B. Retention of a device in a longitudinal fashion is advantageous in situations where you want to restrict the longitudinal movement of the device. As the device is placed into and out of the holding area 14 as shown a restriction of longitudinal movement occurs. That is, a curvature of the device through the holes 14 creates a friction at the edge of the holes thereby a longitudinal restriction force may be utilized to prevent longitudinal movement associated with the weight of the device. The device may still be moved longitudinally, but more force than the weight of the device must be applied. Alternatively, a "T" type channel 13 may be used rather than the curvature as shown in FIG. 2B.

Figure 7:
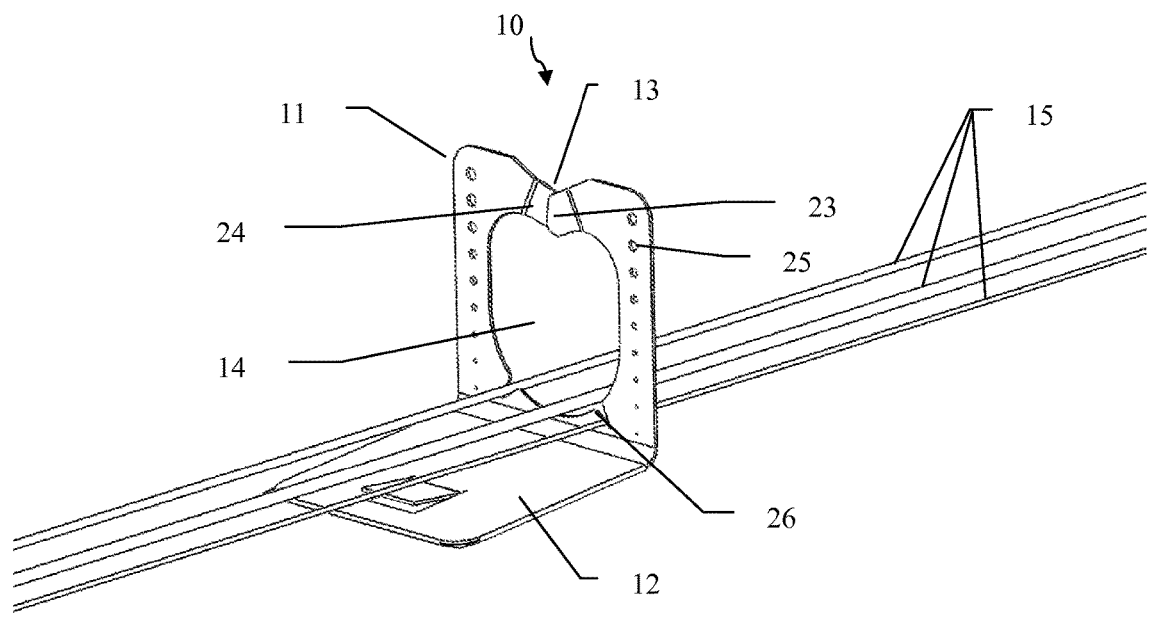
FIG. 7 is a perspective view of another embodiment of the invention.

FIG. 7 shows another embodiment of the invention. Referring to FIG. 7, the retaining device 10 is similar to the embodiment in FIG. 2, but includes some additional features. The retaining device 10 may receive multiple medical devices, e.g., guide wires secured within the holding area 14. The holding portion 10 includes two slots 26, e.g., V-shaped slots, near the bottom edge of the holding area 14. These slots are configured to hold and organize multiple wires 15 within the holding area 14. It is common during interventional procedures to have multiple catheters or guidewires extending from the entry site and it is advantageous to separate them to prevent tangling or to help identify the wire(s).

Figure 8:
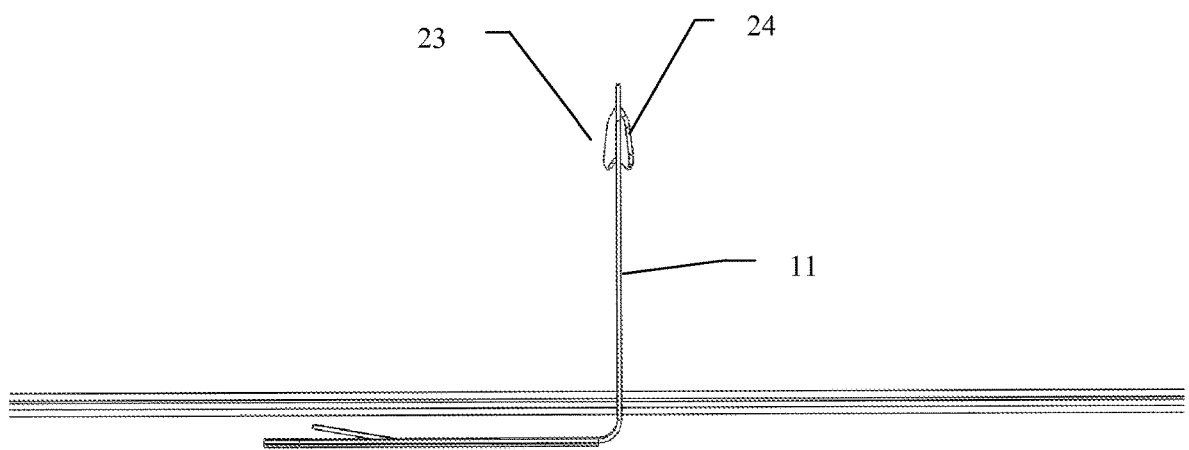
FIG. 8 is a side view of the embodiment shown in FIG. 6.

A plurality of the holes 25 are configured to extend through the holder portion 10. These holes 25 provide multiple functions 1) a trailing end of a wire could be inserted through and looped, 2) the holes can act as measurement gauges for estimating medical device size, and 3) the holes can be used to alter the flexural strength of the holder portion. Another feature shown in FIGS. 7 and 8 is the angled tabs 23 and 24 surrounding the channel 13 on the holder portion 11. Tab 23 on the right side of the channel 13 is angled forward whereas tab 24 on the left side of the channel is angled backward. The purpose of these tabs is to provide easier insertion and removal of the medical device from the holding area and eliminate the need for manual flexing of the holder portion to remove or insert the medical device. Channel width 13 is still smaller than the diameter of the smallest medical device to be used but when a medical device is pushed into the channel the tabs flex themselves to open the channel 13 and at the same time flex the holder portion 11 to further open the channel and permit wire entry. Tab 23 will flex forward and at the same time flex the right side of the holder portion 11 forward whereas tab 24 will flex backward and flex the left side of the holder portion backward to open the channel and permit wire entry. This feature reduces the effort and force required to insert or withdrawal a medical device and would be advantageous in situations where wires are frequently inserted and removed from the holding area.

EXAMPLES

Without intending to limit the scope of the invention, the following examples illustrate how various embodiments of invention may be made and/or used.

Example 1

In this example, a retaining device similar to the device shown in FIG. 2B was fabricated. A rectangular polypropylene sheet being about 1.25 inches by 2 inches and about 0.03 thick was utilized. The corners of this sheet were radiused to about 0.25 inches with cutting shears. Two holes being about 0.25 inches in diameter were punched in the holder portion using a leather punch. The center of each hole was spaced about 0.50 inches from each other and extended from the top edge about 0.38 inches and the side edge at about 0.38 inches. Each side of the loading channel was cut to include about a 0.25 inch radius shear cut extending from the top edge and communicating with the bottom of each hole. In addition, a linear perforated line was punched across the part, parallel to and about 0.75 inches from the top edge using a perforated leather punch to form a living hinge.

A pressure sensitive adhesive with protective liner was cut to match the base portion and adhered to the bottom side of the base. The pressure sensitive adhesive was 3M part no. 1567.

While the foregoing written description of the invention enables one of ordinary skill to make and use what is considered presently to be the best mode thereof, those of ordinary skill will understand and appreciate the existence of variations, combinations, and equivalents of the specific embodiment, method, and examples herein. The invention should therefore not be limited by the above described embodiment, method, and examples, but by all embodiments and methods within the scope and spirit of the invention as claimed.

It will be apparent to those skilled in the art that various modifications and variations can be made in the present invention without departing from the spirit or scope of the invention. Thus, it is intended that the present invention cover the modifications and variations of this invention provided they come within the scope of the appended claims and their equivalents.

What is claimed is:

1. A method of using a retaining device to secure a medical apparatus at a predetermined location during a medical procedure on a patient, comprising:
    providing a retaining device, wherein the retaining device comprises a rectangular shaped material comprising a base portion, a holding portion, and a living hinge separating the base portion from the holding portion, the base portion comprising a first base side and a second base side, wherein the second base side comprises an adhesive material on a surface of the second base side and the base portion is dimensioned to be larger in area than the holding portion, wherein the holding portion, a first holding area and a second holding area coupled to the base portion at a flexible coupled portion comprising the living hinge, wherein the living hinge comprises a linear perforated line across a width of the rectangular shaped material, and wherein the living hinge is configured to permit the holding portion to be arranged at a predetermined angle in a range from about 30 degrees to about 170 degrees relative to the base portion, wherein the holding portion comprising a first side extending from the living hinge to a first top portion, a second side opposite said first side extending from the living hinge to a second top portion, a loading channel arranged between the first side and the second side comprising a V-type shape and configured to be in communication with the first holding area and the second holding area,
    wherein the first top portion comprises a first flexible region arranged around at least a portion of the first holding area and the second top portion comprises a second flexible region arranged around at least a portion of the second holding area;
    attaching the base portion of the retaining device with the adhesive material to a substrate selected from the group consisting of a cloth, medical gown, and surgical drape;
    moving the first flexible region in order to allow access to the first holding area through at least the loading channel;
    arranging at least a portion of the medical apparatus to be used during the medical procedure through the loading channel and opening created by moving the first flexible region into the first holding area which is an internal first closed holding area of the retaining device after the first flexible region returns to an orientation after the arranging step in order to secure the medical apparatus;

moving the second flexible region in order to allow access to the second holding area through at least the loading channel; and arranging at least a portion of the medical apparatus to be used during the medical procedure through the loading channel and opening created by moving the second flexible region into the second holding area which is an internal closed second holding area of the retaining device after the second flexible region returns to an orientation after the arranging step in order to secure the medical apparatus, wherein the medical apparatus is now retained in a substantially longitudinal configuration or substantially parallel configuration along a substantially longitudinal axis extending from first side to the second side.

2. The method of claim 1, wherein the medical apparatus comprises an electrical line.

3. The method of claim 2, further comprising:

providing a second medical apparatus;

moving the second flexible region in order to allow access to the second holding area through at least the loading channel; and arranging at least a portion of the second medical apparatus to be used during the medical procedure through the loading channel and opening created by moving the second flexible region into the second holding area which is an internal closed holding area of the retaining device after the second flexible region returns to an orientation after the arranging step in order to secure the medical apparatus.

4. The method of claim 1, wherein the base portion further comprises an internal portion comprising a flexible tab configured to move from a first locking orientation to a second non-locking orientation, wherein the attaching a retaining device to a substrate step comprises moving the flexible tab from non-locking orientation to a locking orientation in order to releasable couple the retaining device to the substrate.

5. The method of claim 4, wherein the substrate comprises a surgical drape.

6. A method of using a retaining device to secure a medical apparatus during a medical procedure on a patient, comprising:

providing a retaining device comprising a rectangular shaped material comprising a base portion and a holding portion separated from the base portion with a folding or living hinge comprises a plurality of perforations, wherein the holding portion is configured to be arranged at a predetermined angle in a range from about 30 degrees to about 170 degrees relative to the base portion, wherein the holding portion comprising a first side portion extending from the folding or living hinge to a first end portion, wherein the first end portion includes a first flexible tab partially surrounding a first holding area and the holding portion comprises a second side portion extending from the folding or living hinge to a second end portion, wherein the second end portion includes a second flexible tab partially surrounding a second holding area, the first holding area comprises an first internal space including an first internal holding area that is substantially closed, the first internal holding area arranged between the first side portion and second side portion, the second holding area comprises an second internal space including an second internal holding area that is substantially closed, the second internal holding area arranged between the second side portion and first side portion, and a loading channel formed between the first flexible tab and second flexible tab and communicating with the first internal holding area and the second internal holding area, wherein the first internal holding area and the second internal holding area is dimensioned to accept the medical apparatus;

positioning the holding portion at an angle in a range from about 30 degrees to about 170 degrees relative to the base portion;

arranging at least a portion of the medical apparatus comprising one of medical wire, a guide wire, a catheter, an electrical line, a cable, and a tubing in the first internal holding area through the loading channel; and arranging at least a portion of the medical apparatus in the second internal holding area through the loading channel, wherein the medical apparatus is configured in a longitudinal orientation substantially along an axis extending from the first side portion to the second side portion.

7. The method of claim 6, wherein the retaining device further comprises an attachment mechanism; and further comprising attaching the retaining device to a supporting surface with the attachment mechanism, wherein the supporting surface is selected from the group consisting of a cloth, a medical gown, a surgical drape, and a table with the attachment mechanism.

8. The method of claim 7, wherein the attachment mechanism comprises an adhesive.

9. The method of claim 6, wherein the angle is a range from about 80 degrees to about 100 degrees.

10. The method of claim 9, wherein the angle is about 90 degrees.

11. The method of claim 6, wherein the first internal space comprises a circular geometric configuration and the second internal space comprises a circular geometric configuration.

12. A method of using a retaining device to secure a medical apparatus to the retaining device, comprising:

providing a retaining device comprising a rectangular material having a base portion and a holding portion separated from the base portion with a living hinge comprising a linear perforated region configured to permit the holding portion to be arranged at a predetermined angle in a range from about 30 degrees to about 170 degrees relative to the base portion, wherein the holding portion comprises a first side portion and second side portion, the first side portion extending from the living hinge to a first end portion including a first flexible portion partially surrounding a first holding area comprising a first internal space that is substantially closed, the second side portion extending from the living hinge to a second end portion including a second flexible portion partially surrounding a second holding area comprising a second internal space that is substantially closed, and a loading channel arranged at least partially between the first flexible portion and the second flexible portion;

moving the first flexible portion and arranging at least a portion of the medical apparatus in the first internal space through the loading channel; and moving the second flexible portion and arranging at least a portion of the medical apparatus in the second internal space through the loading channel, and wherein the medical apparatus is arranged in an orientation that is substantially parallel to an axis extending from the first side portion to the second side portion.

13. The method of claim 12, wherein the living hinge allows the holding portion to move from a first position to a second position different than the first position relative to the base portion.

14. The method of claim 12, wherein the retaining device comprises a material selected from the group consisting of a thermoplastic, metal, alloy and combinations thereof.

15. The method of claim 12, wherein the medical apparatus comprises a medical guidewire.

16. The method of claim 12, wherein the retaining device further comprises an attachment mechanism.

17. The method of claim 16, wherein the attachment mechanism comprises an adhesive material.

18. The method of claim 12, wherein the holding portion further comprises a plurality of holes.

19. The method of claim 12, wherein the rectangular material comprises a thickness of about 0.03 inches.

20. The method of claim 12, wherein the rectangular material comprises an area in range from about 5 inches$^2$ to about 28 inches$^2$.

\* \* \* \* \*